United States Patent [19]

Clark

[11] 4,379,165

[45] Apr. 5, 1983

[54] ANTI-CONVULSANT

[75] Inventor: Charles R. Clark, Auburn, Ala.

[73] Assignee: Research Corporation, New York, N.Y.

[21] Appl. No.: 264,604

[22] Filed: May 18, 1981

[51] Int. Cl.³ .................... C07C 103/75; A61K 31/16
[52] U.S. Cl. .................................. 424/324; 564/163; 564/168
[58] Field of Search ................. 564/163, 168; 424/324

[56] References Cited

U.S. PATENT DOCUMENTS

| | | | |
|---|---|---|---|
| 2,161,628 | 6/1939 | Matthieu et al. | 564/168 |
| 3,657,219 | 4/1972 | Ronco et al. | 564/168 |
| 4,284,813 | 8/1981 | Takematsu et al. | 564/168 |

OTHER PUBLICATIONS

Chem. Abstracts, 9th index, pp. 2897CS, 2883CS, 2888CS.

*Primary Examiner*—Arthur P. Demers
*Attorney, Agent, or Firm*—Shoemaker and Mattare, Ltd.

[57] ABSTRACT

New amino-benzamides and their use for the treatment of epilepsy.

5 Claims, No Drawings

ANTI-CONVULSANT

BACKGROUND OF THE INVENTION

1. Field of the Invention

This invention relates to a new type of anti-convulsant drug. Specifically, it deals with new benzamide compounds and their use for the treatment of epilepsy.

2. Description of the Prior Art

In the treatment of epilepsy or other convulsing causing diseases, various drugs, such as Phenobarbital, Phenytoin, Mephenytoin, and Carbamazapine have been used to prevent their attacks. These drugs, however, have undesirable side-effects in most cases.

There is, therefore, a need for a new type of anti-convulsant drug which will have fewer side-effects than those presently used.

BRIEF SUMMARY OF THE INVENTION

It is, accordingly, one object of the present invention to set forth a new anti-convulsant drug.

Another object of the present invention is to set forth new drugs of the amino-benzamide type for the treatment of epilepsy which have fewer side-effects.

A still further object of the present invention is to set forth new amino-benzamide anti-convulsant drugs and method for using the same for the treatment of epilepsy.

These and other advantages of the present invention will be apparent from the following detailed description and test data.

In accordance with the above objects, it has been found that amino-benzamide compounds are capable of preventing convulsing attacks caused by epilepsy. These compounds are various ortho, meta, and para amino-benzamides. These compounds are:

1. 4-amino-N-phenyl-benzamide; [4-aminobenzanilide]
2. 4-amino-N-cyclohexyl-benzamide
3. 4-amino-N-amyl-benzamide; [4-amino-N-(n-pentyl)-benzamide]
4. 4-amino-N-benzyl-benzamide
5. 4-amino-N,N-(di-n-propyl)-benzamide
6. 4-amino-N-(n-hexyl)-benzamide
7. 4-amino-N-(n-butyl)-benzamide
8. 4-amino-N-(N-methylbenzyl)-benzamide

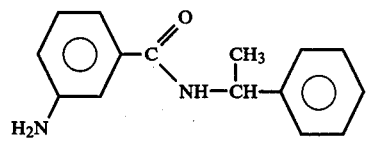

Name: 3-amino-N—(alpha-methylbenzyl)-benzamide; [m-amino-N—alpha-methylbenzyl)-benzamide]

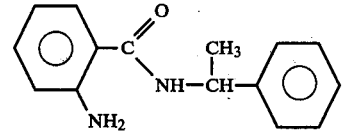

Name: 2-amino-N—(alpha-methylbenzyl)-benzamide; [o-amino-N—(alpha-methylbenzyl)-benzamide]

11. 4-amino-N-(alpha-methylbenzyl)-benzamide

With the drugs available today, complete control of epilepsy can be achieved in about 60% of epilepsy cases. These amino-benzamides represent a new class of compounds for the treatment of epilepsy. The highly potent anti-convulsant activity of 4-amino-N-(alpha-methylbenzyl)-benzamide offers some unique advantages over currently available drugs. In animal studies, this amino-benzamide is effective against a wide range of convulsion types. This activity range is broader than many of the currently available drugs. Additionally, the amide offers a wide margin of safety between the dose required to produce anti-convulsant effects and the dose which produces any central nervous system side-effects. These facts all indicate that the amino-benzamides have the potential to improve the current drug therapy for epilepsy.

DETAILED DESCRIPTION OF THE PREFERRED EMBODIMENTS

The following equations illustrate the formation of the benzamide compounds of the present invention and their use using 4-amino-N-(alpha-methylbenzyl)-benzamide as an example:

PREPARATION

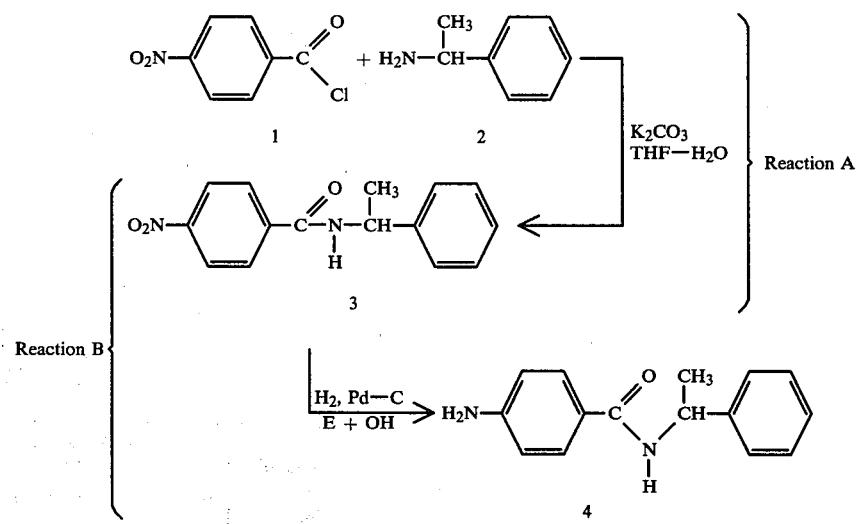

The initial step (reaction A) involves the formation of the amide bond and the final reaction (B) is the conversion of the aromatic nitro-group to the desired amino-group.

Reaction A

A 1 L. 3-necked flask was equipped with a magnetic stir bar, reflux condensor with a drying tube, a pressure equalizing addition funnel, and a heating mantle. A 200-ml portion of 20% aqueous potassium carbonate was added to the flask followed by 10 g (0.083 mole) of d,l-alpha-methylbenzylamine (#2) in 200-ml of tetrahydrofuran. The resulting mixture was stirred and a solution of 23.3 g (0.125 mole) of 4-nitrobenzoylchloride (#1) in 100-ml of tetrahydrofuran was added dropwise from the addition funnel. Upon completion of the addition, the reaction mixture was heated to reflux for 12 hours then cooled and extracted 3 times with 100-ml portions of chloroform. The chloroform extracts were combined, dried over magnesium sulfate and evaporated to yield the desired compound, 4-nitro-N(alpha-methylbenzyl)-benzamide (#3). Recrystallization from benzene produced the purified compound.

Reaction B

A solution of 5 g (0.018 mole) of 4-nitro-N(alpha-methylbenzyl)-benzamide (#3) in 200-ml of absolute ethanol was added to a Paar hydrogenation bottle. To the solution was added a 0.4 g sample of 5% palladium on charcoal and the bottle placed on a Paar low-pressure hydrogenation apparatus. The mixture was shaken at room temperature in the presence of 45 p.s.i. of hydrogen for 2.5 hours. The catalyst was then removed by filtration through celite and the ethanol evaporated to yield the desired compound, 4-amino-N-(alpha-methylbenzyl)-benzamide (#4). Recrystallization from benzene produced the compound in pure form.

ADMINISTRATION

The anti-convulsant amide (4) was administered to mice and rats as a solution. The solution was prepared by dissolving the compound in 30% polyethylene glycol 400. The compound was injected either orally or intraperitoneally in a volume of 0.01 ml/g body weight in mice and 0.04 ml/10 g body weight in rats.

The amide is the only compound dissolved in the polyethylene glycol 400 solvent, thus the anti-convulsant activities observed do not depend on specific proportions of components. The use of the compound as a solution is only for ease of administration to animals and the activity observed is not based on the fact that the compound is in a solution. This is further pointed out by the fact that the solvent (30% polyethylene glycol 400) alone was used as a control in these studies (i.e., administration of the same volumes of solvent only produced no anti-convulsant effects).

ANTI-CONVULSANT ACTIVITY

The anti-convulsant activity of this compound (4-amino-N-(alpha-methylbenzyl)-benzamide) is based on results obtained from testing procedures in mice and rats. The anti-convulsant amide was compared with four prototype anti-epileptic agents (phenobarbital, phenytoin, mephenytoin and carbamazepine). The profile of anti-convulsant activity for each substance was established by five tests: one electrical and four chemical. The electrical test employed was the maximal electroshock seizure (MES) pattern test. The four chemical tests included the subcutaneous Metrazol Seizure Threshold Test (sc Met), subcutaneous Bicuculline Seizure Threshold Test (sc Bic), subcutaneous Picrotoxin Seizure Threshold Test (sc Pic), and the subcutaneous Strychnine Seizure Pattern Test (sc Strych). These tests are conducted by administering the anti-convulsant compound or drug to the animals then giving the convulsive amount of electrical energy or chemical convulsant and measuring the ability of the test compound to prevent the production of convulsions.

To determine anti-convulsant potency and toxicity, groups of at least eight mice were tested with various doses of the drug until at least four points were established between the limits of 100% protection or toxicity and 0% protection or toxicity. The dose of drug required to produce the desired endpoint in 50% of animals (ED50), 95% confidence interval, slope of the regression line, and the standard error of the slope were then calculated.

The activity data comparing compound 4 with the four prototype anti-convulsant drugs are given in the following Tables. These data were obtained in testing conducted by the Anticonvulsant Drug Development Program, Epilepsy Branch, Neurological Disorders Program, National Institute of Neurological and Communicative Disorders and Stroke. The tests used are described in J. F. Reinhard and J. F. Reinhard, Jr., "Experimental Evaluation of Anticonvulsants," in Anticonvulsants, J. A. Vida, Ed., Academic Press, New York, N.Y., 1977.

In order to better understand the terminology in the tables, the following definitions of terms therein are set forth.

Description of Data Terms (a) MES=Maximal electroshock seizure test. This test measures the ability of the test drug to abolish the hind-limb tonic-extensor component of maximal seizures induced by 50 mA of current delivered to the animals for 0.2 seconds.

(b) scMet=Subcutaneous metrazol seizure threshold test. The test measures the ability of the test drug to afford complete protection against a subcutaneously administered convulsant dose of metrazol. Metrazol is a very potent CNS stimulant which in sufficient doses produces convulsions.

(c) scBic=Subcutaneous bicuculline seizure threshold test. Explanation same as in (b).

(d) scPic=Subcutaneous picrotoxin seizure threshold test. Explanation same as in (b)

(e) ScStrych=Subcutaneous strychnine seizure pattern test. The test measures the ability of the test drug to abolish all toxic components of seizures induced by the subcutaneous injection of a convulsant dose of strychnine.

(f) ED50=Effective dose in 50% of the subjects (median effective dose), the dose of the drug in mg/kg of animal weight required to produce the pharmacological effect in 50% of the animals in a group.

(g) TD50=Toxic dose in 50% of the subjects, dose required to produce toxic side-effects in 50% of the animals tested. The test for toxic effects is referred to as the "Rotorod Toxicity Test." The test shows the loss of an animal's ability to maintain its balance on a rotating rod. Untreated or normal animals can easily maintain their balance in this test.

(h) HD50=Hypnotic dose in 50% of the subjects tested. Hypnosis is defined as loss of righting reflex- —when placed on its back, the animal does not have the ability to get to its feet.
(i) LD50=Lethal dose in 50% of the subjects, the dose required to kill 50% of the animals.
(j) PI=Protective index, defined as the ratio of TD50 to ED50 (TD50/ED50). The PI is a measure of the safety of the drug. A high PI value indicates a greater margin of safety between the effective dose for the pharmacological effect and the toxic dose producing side-effects. A compound with a high PI would be a safer drug to use.
(k) 95% Confidence Interval—This is a statistical term which says that if we repeated a given test a number of times, 95% of the time the result would lie within the limits defined as the 95% confidence interval. Example: From Table 1 the ED50 for 4-amino-N-(alpha-methylbenzyl)-benzamide in the MES test is given as 18.02 mg/kg. If we were to repeat this test 100 times, the ED50 which we would determine would fall between 13.41–21.43 mg/kg 95% of the time. The 95% confidence interval then represents a range of doses.
(l) Slope of regression line—This represents the rate of change in response (effect) for a change in dose. The higher the numerical value of the slope, the greater the rate of change in response.

TABLE 1.

Profile of Anti-convulsant Activity of Intraperitoneally Administered 4-amino-N—(alpha-methylbenzyl)-benzamide and Some Prototype Anti-epileptic Drugs in Mice

| ADD No. Substance | Time of Test (hrs) | Rotorod TD50 (mg/kg) | ED50 (mg/kg) and PI | | | |
|---|---|---|---|---|---|---|
| | | | MES | | sc Met | |
| 4-amino-N—(alpha-methylbenzyl)-benamide | 1, ½, ½ | 170.78 (153.82–189.96) [15.32] | 18.02 (13.41–21.43) [6.02] | 9.48* | 41.72 (38.83–46.00) [13.67] | 4.09* |
| Phenobarbital | ½, 1, 1 | 69.01 (62.84–72.89) [24.67] | 21.78 (14.99–25.52) [14.98] | 3.17 | 13.17 (5.87–15.93) [5.93] | 5.24 |
| Phenytoin | 2,2 | 65.46 (52.49–72.11) [15.23] | 9.50 (8.13–10.44) [13.67] | 6.89 | No protection up to 300 | <0.22 |
| Mephenytoin | ½, ½, ½ | 153.82 (132–178.73) [9.22] | 60.50 (49.45–70.25) [8.01] | 2.54 | 30.45 (19.67–39.47) [4.76] | 5.05 |
| Carbamazepine | ½, ½ | 71.56 (45.91–134.79) [4.77] | 8.81 (5.45–14.09) [3.62] | 8.12 | No protection up to 100 | <0.72 |

( ) 95% Confidence interval
[ ] Slope, regression line
*Protection Index (P.I.) = TD50/ED50

As can be seen from the above table, 4-amino-N-(alpha-methylbenzyl)-benzamide has an ED50 of 18.02 mg/kg as measured against maximal electroshock seizures following intraperitoneal (ip) administration in mice and an ED50 of 41.72 mg/kg against SC metrozole. The compound shows a similar level of activity in these tests in rats. The rotorod toxicity of the compound as measured following ip administration in mice is TD50=170.78 mg/kg. This produces a protective index (PI=TD50/ED50) of 9.48 for ip administration in mice. This PI is higher than that for four standard drugs commonly used in anti-convulsant therapy: phenobarbital, PI=3.17; phenytoin, PI=6.89; mephenytoin, PI=2.54; and carbamazepine, PI=8.12.

TABLE 2.

Profile of Acute Neurotoxicity of 4-amino-N—(alpha-methylbenzyl)-benzamide and Some Prototype Anti-epileptic Drugs in Mice

| ADD No. or Name | Profile of Acute Toxicity, Mice l.p. | | | HD50 LD50* (mg/kg) |
|---|---|---|---|---|
| | 1 × TD50 | 2 × TD50 | 4 × TD50 | |
| 4-amino-N—(alpha-methylbenzyl)-benzamide | (171 mg/kg) At 30 min, both animals had decreased motor activity and ataxia; one was spastic, toxic by rotorod test, cyanotic, and had decreased respiration. Both animals appeared normal by 8 hrs. | (342 mg/kg) Both animals had decreased motor activity, ataxia, rotorod toxicity, muscle relaxation, cyanosis, and decreased respiration at 30 min; one had spasticity, sedation, ptosis, muscle relaxation and loss of righting reflex at 1 hr. This animal regained righting reflex at 4 hrs. Both animals appeared normal at 24 hrs. | (684 mg/kg) At 1 hr both animals had decreased motor activity, ataxia, rotorod toxicity, sedation, ptosis, muscle relaxation, loss of righting reflex, decreased respiration and cyanosis; one was spastic. At 6 hrs one was hypnotic, analgesic and anesthetized; at 24 hrs this animal was dead while the other animal appeared normal. | 461.76 (421.03–495.04) [20.85] 718.18 (691.28–742.98) [36.24] |
| Phenobarbital | (70 mg/kg) Ataxia with increased motor activity followed by sedation and | (140 mg/kg) Ataxia with increased motor activity followed by loss of righting reflex, tremors, reflex | (260 mg/kg) Ataxis with increased motor activity followed by loss of righting | 135.45 (114.90–177.42) [8.41] |

TABLE 2.-continued
Profile of Acute Neurotoxicity of 4-amino-N—(alpha-methylbenzyl)-benzamide and Some Prototype Anti-epileptic Drugs in Mice

| ADD No. or Name | Profile of Acute Toxicity, Mice I.p. | | | HD50 LD50* (mg/kg) |
|---|---|---|---|---|
| | 1 × TD50 | 2 × TD50 | 4 × TD50 | |
| | ptosis with one of two animals toxic by the rotorod test up to 4 hrs. | scratching, ptosis, sedation and some respiratory depression. Both mice regained their righting reflex at 2 hrs and one was still toxic by the rotorod test at 8 hrs | reflex, tremors, reflex scratching, ptosis, sedation anesthesia with analgesic and respiratory depression. Both animals became cold to touch and cyanotic with increased respiratory depression with death at approximately 3 and 6 hrs. | 264.70 (241.55-285.52) [15.95] |
| Phenytoin | (65 mg/kg) Increased motor activity, slight ataxia, frequent grooming, nervous behavior, & straub tail. Animals were not toxic by the rotorod test. | (130 mg/kg) Mild ataxia, periods of sedation, spasms of arching, rolling, straub tail, ptosis, & respiratory depression. Later, spasms reduced & sedation increased. At 24 hrs, toxicity present, other symptoms less pronounced. | (260 mg/kg) Toxic manifestations identical to 2TD50's. At 1 hr righting reflex absent, longer periods of sedation, & spasms reduced to head twisting & uncoordinated movements; respiratory depression continued, mice dead at 24 hrs. | 178.34 (152.93-195.45) [14.03] 229.61 (216.44-259.10) [15.89] |
| Mephenytoin | (154 mg/kg) Both animals were ataxic and had decreased respiration. Both animals appeared normal at 8 hrs. | (308 mg/kg) Both animals were ataxic and toxic by rotorod, had decreased motor activity, decreased respiration and cyanosis. Both animals appeared normal at 24 hrs. | (616 mg/kg) Both animals had decreased motor activity, ataxia, rotorod toxicity, sedation, ptosis, muscle relaxation and cyanosis. These symptoms, except for anesthesia and analgesia, were still present in one animal after 24 hrs. The other animal was normal at 24 hrs. | 405.97 (366.67-453.67) [17.00] 567.97 (504.15-640.18) [9.80] |
| Carbamazepine | (70 mg/kg) Mild ataxia with one of two animals toxic by the rotorod test. Normal within 1 hr. | (140 mg/kg) Sedation followed by depressed respiration with normal respiration and mild ataxia returning at 2 hrs. | (280 mg/kg) Marked ataxia, hing legs spread, respiratory depression, loss of righting reflex, ptosis, hypnosis without analgesia, retention of corneal reflex, righting reflex regained at 2 hrs. No deaths at 24 hrs. | 172.24 (134.12-197.79) [5.92] 628.70 (555.77-707.61) |

*24-hour period

TABLE 3.
Profile of Anti-convulsant Activity of Orally Administered 4-amino-N—(alpha-methylbenzyl)-benzamide and Some Prototype Anti-epileptic Drugs in Mice

| ADD No. Substance | Time of Test (hrs) | Rotorod TD50 (mg/kg) | ED50 (mg/kg) and PI | | | |
|---|---|---|---|---|---|---|
| | | | MES | | sc Met | |
| 4-amino-N—(alpha-methylbenzyl)-benzamide | 2, ½, ¼ | 271.21 (239.67-301.27) [9.09] | 47.66 (45.11-50.13) [24.79] | 5.69* | Maximum 25% Protection at 100 & no protection at 300 | <0.90* |
| Phenobarbital | 2, 2, 2 | 96.78 (79.88-115.00) [8.51] | 20.09 (14.78-31.58) [5.20] | 4.82 | 12.59 (7.99-19.07 [3.84] | 7.69 |
| Phenytoin | 2, 2 | 86.71 (80.39-96.09) [13.01] | 9.04 (7.39-10.62) [6.28] | 9.59 | No protection up to 300 | <0.29 |
| Mephenytoin | 4, 2, ½ | 353.93 (291.31-412.36) [6.58] | 65.87 (63.80-68.25) [28.81] | 5.37 | 36.31 (25.79-48.25) [3.60] | 9.75 |
| Carbamazpine | ½, ½, 2 | 217.21 (131.49-270.11) [3.47] | 15.44 (12.44-17.31) [9.07] | 14.06 | 48.07 (40.75-57.35) [5.50] | 4.52 |

( ) 95% Confidence Interval
[ ] Slope, regression line
*Protective Index (P.I.) = TD50/ED50

TABLE 4.

Anti-convulsant Potency of Intraperitoneally
Administered 4-amino-N—(alpha-methylbenzyl)-
benzamide and Some Prototype Anti-epileptic Drugs
As Measured by Ability to Prevent Chemically-
Induced Seizures in Mice

| ADD No. Substance | Time of Test (hrs) | Rotorod TD50 (mg/kg) | ED50 (mg/kg) and PI | | | | | | | |
|---|---|---|---|---|---|---|---|---|---|---|
| | | | sc Met | | Bicuculline | | Picrotoxin | | Strychnine | |
| 4-amino-N—(alpha-methylbenzyl)-benzamide | ½, ½, ¼ | 170.78 (153.82–189.96) [15.32] | 41.72 (38.83–46.00) [13.67] | 4.09* | 39.07 (20.27–61.57) [2.38] | 4.37* | 191.23 (84.48–724.71) [1.73] | 0.89* | Maximum protection of 37.5% at 170; 25% at 200 | <0.85* |
| Pheno-barbital | ½, 1 | 69.01 (62.84–72.89) [24.67] | 13.17 (5.87–15.93) [5.93] | 5.24 | 37.72 (26.49–47.39) [4.07] | 1.83 | 27.51 (20.88–34.82) [4.79] | 2.51 | 95.30 (91.31–99.52) [18.51] | 0.72 |
| Phenytoin | 2, 2 | 65.46 (52.49–72.11) [15.23] | No protection up to 100 | <0.22 | No protection up to 100 | <0.65 | No protection up to 100 | <0.65 | Max. Prot. 50% at 55–100 | |
| Mephenytoin | ½, ¼ | 153.82 (132.86–178.73) [9.22] | 30.45 (19.67–39.47) [4.76] | 5.05 | 124.14 (84.10–188.49) [1.99] | 1.24 | 100.96 (79.34–122.92) [7.43] | 1.52 | Max. Prot. 50% at 70–150 | |
| Carbamaz-epine | ½, ¼ | 71.56 (45.91–134.79) [4.77] | No protection up to 100 | <0.72 | 100 mg/kg ½ protected | <0.72 | 37.20 (25.32–59.69) [3.86] | 1.92 | 78.83 (39.39–132.03) [2.85] | 0.91 |

( ) Confidence Levels, 95%
[ ] Slope, regression line
*Protective Index (P.I) = TD50/ED50

TABLE 5.

Profile of Anti-convulsant Activity of Orally
Administered 4-amino-N—(alpha-methylbenzyl)-
benzamide and Some Prototype Anti-epileptic
Drugs in Mice

| ADD No. Substance | Time of Test (hrs.) | Rotorod TD50 (mg/kg) | ED50 (mg/kg) and PI | | | |
|---|---|---|---|---|---|---|
| | | | MES | | sc Met | |
| 4-amino-N—(alpha-methyl-benzyl)-benzamide | 2, 1, 1 | 170.08 (129.74–205.75) [5.66] | 16.11 (15.08–17.46) [19.24] | 10.56* | Max. Prot. 50% at 300; 1 of 8 animals, recurring clonic seizures** | * |
| Pheno-barbital | ½, 5, 5 | 61.09 (43.72–95.85) [3.00] | 9.14 (7.58–11.86) [4.12] | 6.68 | 11.55 (7.74–15.00) [4.08] | 5.29 |
| Phenytoin | ½, 4 | >3000 | 29.82 (21.92–38.91) [2.82] | >100 | No protection up to 800 | |
| Mephenytoin | 4, 2, 4 | 85.73 (69.88–93.76) [13.47] | 18.10 (14.02–24.91) [3.60] | 4.74 | 21.65 (17.99–25.77) [8.43] | 3.96 |
| Carbamaz-epine | 2, 1 | 813.06 (488.76–1233.87) [6.06] | 8.50 (3.39–10.53) [4.50] | 95.65 | Variable | |

( ) Confidence Levels, 95%
[ ] Slope, regression line
*Protective Index (P.I.) = TD50/ED50
**After intraperitoneal administration, 150 mg/kg, 8/8 protected vs sc Met test and 6/8 toxic; 75 mg/kg, 4/8 protected vs sc Met test and 2/8 toxic.

TABLE 6.

Profile of Anti-convulsant Activity of Intraperitoneally
Administered 4-amino-N—(alpha-methylbenzyl)-benzamide and
Some Prototype Anti-epileptic Drugs in Mice

| ADD No. Substance | Time of Test (hrs) | Rotorod TD50 (mg/kg) | ED50 (mg/kg) and PI | | | | | | | |
|---|---|---|---|---|---|---|---|---|---|---|
| | | | MES | | sc Met | | Bicuculline | | Picrotoxin | Strychnine |
| 4-amino-N—(alpha- | 1, ½ | 170.78 (153.82– | 18.02 (13.41–21.43) | 9.48* | 41.72 (38.46.00) | 4.09* | 39.07 (20.27– | 4.37* | 191.23 (84.48– | 0.89* Max Prot 37.5% at |

TABLE 6.-continued

Profile of Anti-convulsant Activity of Intraperitoneally Administered 4-amino-N—(alpha-methylbenzyl)-benzamide and Some Prototype Anti-epileptic Drugs in Mice

| ADD No. Substance | Time of Test (hrs) | Rotorod TD50 (mg/kg) | ED50 (mg/kg) and PI | | | | | | | | |
|---|---|---|---|---|---|---|---|---|---|---|---|
| | | | MES | | sc Met | | Bicuculline | | Picrotoxin | | Strychnine |
| methylben-zyl)-ben- | ½ | 189.96) [15.32] | [6.02] | | [13.67] | | 61.57) [2.38] | | 724.71) [1.73] | | 170 |
| Pheno-barbital | ½, 1, 1 | 69.01 (62.84–72.89) [24.67] | 21.78 (14.99–25.52) [14.98] | 3.17 | 13.17 (5.87–15.93) [5.93] | 5.24 | 37.72 (26.49–47.39) [4.07] | 1.83 | 27.51 (20.88–34.82) [4.79] | 2.51 | 95.30 (91.31–99.52) [18.51] |
| Phenytoin | 2, 2 | 65.46 (52.49–72.11) [15.23] | 9.50 (8.13–10.44) [13.66] | 6.89 | No protection up to 300 | <0.22 | No protection up to 100 | <0.65 | No protection up to 100 | <0.65 | Max. Prot. 50% at 55–100 |
| Mepheny-toin | ½, ½ | 153.82 (132.86–178.73) [9.22] | 60.50 (49.45–70.25) [8.01] | 2.54 | 30.45 (19.67–39.47) [4.76] | 5.05 | 12.414 (84.10–188.49) [1.99] | 1.24 | 100.96 (79.34–122.92) [7.43] | 1.52 | Max. Prot. 50% at 70–150 |
| Carbamaz-epine | ½, ½ | 71.56 (45.91–134.79) [4.77] | 8.81 (5.45–14.09) [3.62] | 8.12 | No protection up to 100 | <0.72 | Max. Prot. 62.5% at 50–130 | | 37.20 (25.32–59.69) [3.86] | 1.92 | 78.83 (39.39–132.03) [2.85] | 0.91 |

( ) 95% Confidence Interval
[ ] Slope, regressling line
*Protective Index (P.I.) = TD50/ED50

TABLE 7.

Profile of Anti-convulsant Activity of Orally Administered 4-amino-N—(alpha-methylbenzyl)-benzamide and Some Prototype Anti-epileptic Drugs in Mice and Rats

| ADD No. Substance | Time of Test (hrs) | | Rotorod TD50 | | MES-ED50 (mg/kg) | | | | sc Met-ED50 (mg/kg) | | | |
|---|---|---|---|---|---|---|---|---|---|---|---|---|
| | Mice | Rats | Mice | Rats | Mice | | Rats | | Mice | | Rats | |
| 4-amino-N—(alpha-methylben-zyl)-benzy-amide | 2, ½, ½ | 2, 1, 1 | 271.21 (239.67–301.27) [9.09] | 170.08 (129.74–205.75) [5.66] | 47.66 (45.11–50.13) [24.79] | 5.69* | 16.11 (15.08–17.46) [19.24] | 10.56* | Maximum 25% Protection at 100 & No Prot. at 300 | | Max. Prot. 50% at 300 1 of 8 animals recurring clonic seizures | |
| Pheno-barbital | 2, ½, 2 | ½, 5, 5 | 96.78 (79.88–115.00) [8.51] | 61.09 (43.72–95.85) [3.00] | 20.09 (14.78–31.58) [5.20] | 4.82 | 9.14 (7.58–11.86) [4.12] | 6.68 | 12.59 (7.99–19.07) [3.84] | 7.69 | 11.58 (7.74–15.00) [4.08] | 5.29 |
| Phenytoin | 2, 2 | ½, 4 | 86.71 (80.39–96.09) [13.01] | >3000 | 9.04 (7.39–10.62) [6.28] | 9.59 | 29.82 (21.92–38.91) [2.82] | >100 | No protection up to 300 | <0.29 | No protection up to 800 | |
| Mepheny-toin | 4, 2, ½ | 4, 2, 4 | 353.93 (291.31–412.36) [6.58] | 85.73 (69.88–93.76) [13.47] | 65.87 (63.80–68.25) [28.81] | 5.37 | 18.10 (14.02–24.91) [3.60] | 4.74 | 36.31 (25.79–48.25) [3.60] | 9.73 [8.43] | 21.65 (17.99–25.77) | 3.96 |
| Carbamaz-epine | ½, ½ | 2, 1 | 217.21 (131.49–270.11) [3.47] | 813.06 (488.76–1233.87) [6.06] | 15.44 (12.44–17.31) [9.07] | 14.06 | 8.50 (3.39–10.53) [4.50] | 95.65 | 48.07 (40.75–57.35) [5.50] | 4.51 | Variable | |

( ) 95% Confidence Interval
[ ] Slope, regression line
*Protective Index (P.I.) = TD50/ED50

TABLE 8.

Quantitative Toxicity Profile of Intraperitoneally Administered 4-amino-N—(alpha-methylbenzyl)-benzamide and Some Prototype Anti-epileptic Drugs in Mice

| Add No. Substance | Time of Test (hrs) | Dose 50 (mg/kg) | | | | |
|---|---|---|---|---|---|---|
| | | Lethality | | Righting Reflex | | Rotorod |
| 4-amino-N—(alpha-methylben-zyl)-benz- | 24, 4, 1 | 718.18 (691.28–742.98) [36.24] | | 461.76 (421.03–495.04) [20.85] | 1.56* | 170.78 (153.82–189.96) [15.32] | 4.21* |

TABLE 8.-continued

Quantitative Toxicity Profile of Intraperitoneally Administered 4-amino-N—(alpha-methylbenzyl)-benzamide and Some Prototype Anti-epileptic Drugs in Mice

| Add No. Substance | Time of Test (hrs) | Lethality | Righting Reflex | | Rotorod | |
|---|---|---|---|---|---|---|
| amide | | | | | | |
| Phenobarbital | 24, 1, ½ | 264.70 (241.55–285.52) [15.95] | 135.45 (114.90–177.42) [8.41] | 1.95 | 69.01 (62.84–72.89) [24.67] | 3.84 |
| Phenytoin | 24, 12, 2 | 229.61 (216.44–259.10) [15.89] | 178.34 (152.93–195.45) [14.03] | 1.29 | 65.46 (52.49–72.11) [15.23] | 3.51 |
| Mephenytoin | 24, 1, ½ | 567.97 (504.15–640.18) [9.80] | 405.97 (366.67–453.67) [17.00] | 1.40 | 153.82 (132.86–178.73) [9.22] | 3.69 |
| Carbamazepine | 24, ½, ¼ | 628.70 (555.77–707.67) [10.11] | 172.24 (134.12–197.79) [5.92] | 3.65 | 71.56 (45.96–134.73) [4.77] | 8.79 |

( ) 95% Confidence interval
[ ] Slope, regression line
*Ratio LD50/HD50 or LD50/TD50

For a compound to be useful in man, it should be adequately absorbed after oral administration and should have an adequate margin of safety. The extent of oral absorption can be determined from the ratio of the oral ED50/i.p. (intraperitoneally) ED50 for a desired pharmacologic activity and should be equal to or less than four for adequate absorption. The available data on the MES test in mice yield an oral ED50/i.p. ED50 of 2.65. This suggests that the amide is adequately absorbed in mice after oral administration.

The amide was examined for mutagenic activity in a series of in vitro microbial assays employing Salmonella indicator organisms. The compound was tested directly and in the presence of liver microsomal enzyme preparations from Aroclor-induced rats. The dose range employed for the evaluation was from 1.0 ug to 10,000.0 ug per plate. The results of the tests conducted on the amide in the absence of a metabolic activation system and in the presence of a rat liver activation system were negative. The amide did not exhibit genetic activity in any of the assays conducted in this evaluation.

As can be seen from the above tests, a critical comparative study of the toxicity and anti-convulsant activity of 4-amino-N-(alpha-methylbenzyl)-benzamide has been done by a battery of tests in mice and rats. The results obtained have been compared with similar data for four prototype clinically useful anti-epileptic drugs: phenobarbital, phenytoin, mephenytoin, and carbamazepine. Based on this critical comparison, it has been concluded that:

1. This amide (4-amino-N-(alpha-methylbenzyl)-benzamide) exhibits anti-convulsant activity in mice and rats as measured by ability to abolish the toxic-extensor phase of maximal electroshock seizures and, after intraperitoneal administration, to elevate minimal Metrazol seizure threshold.

2. This amide is also effective against seizures induced by bicuculline; it is effective against picrotoxin seizures in toxic doses, and only partially effective against seizures induced by strychnine (maximum protection of 37.5% with a minimal toxic dose of 170 mg/kg).

3. Observational assessment of toxic symptoms induced by 1TD50, 2TD50's, 4TD50's for this amide indicate the following are most prominent: decreased motor activity, ataxia, rotorod toxicity, muscle relaxation, and loss of righting reflex. Decreased respiration, cyanosis, and spasticity were also seen in some animals. All surviving animals (one animal given 4TD50's was dead at 24 hours) were free of overt toxic effect within 24 hours after drug administration.

4. Protective indices indicate that this amide has an adequate TD50/ED50 ratio. Intraperitoneal P.I.'s (TD50/ED50) in mice for this amide phenobarbital, phenytoin, mephenytoin, and carbamazepine by the MES test are 9.48, 3.17, 6.89, 2.54, and 812, respectively, and by the sc Met test are 4.09, 5.24, <0.22, 5.05, and <0.72, respectively; after oral administration in rats, the P.I.'s by the MES test are 10.5, 6.68, >100, 4.74, and 95.65, respectively, the only prototype agents with significant P.I.'s by the sc Met test are phenobarbital and mephenytoin (5.29 and 3.96, respectively). Thus, the P.I.'s by the MES test for this amide are within the range of those for the comparative prototype agents.

5. The slopes of the regression lines for this amide by the MES, rotorod, and righting reflex tests resemble those for one or more of the prototype agents. The regression line of this amide by the MES test resembles that for mephenytoin; that by the rotorod test, phenytoin; and that by the righting reflex test, phenytoin and mephenytoin. The slopes of the regression lines by the sc Met and 24-hour lethality tests do not resemble those for any of the prototype agents.

6. The ratio between the oral ED50 and i.p. ED50, determined by the MES test in mice, is 2.65. Thus, it would appear that the test compound is adequately absorbed after oral administration in this species.

7. The results presented show that this amide has significant anti-epileptic potential and the anti-convulsant profile resembles that of phenobarbital and mephenytoin.

Some further compounds of the amino-benzamide type contemplated within this invention are the following:

1. 4-amino-N-phenyl-benzamide; [4-aminobenzanilide]
2. 4-amino-N-cyclohexyl-benzamide
3. 4-amino-N-amyl-benzamide; [4-amino-N-(n-pentyl)-benzamide]
4. 4-amino-N-benzyl-benzamide
5. 4-amino-N,N-(di-n-propyl)-benzamide
6. 4-amino-N-(n-hexyl)-benzamide 7. 4-amino-N-(n-butyl)-benzamide
8. 4-amino-N-(N-methylbenzyl)-benzamide

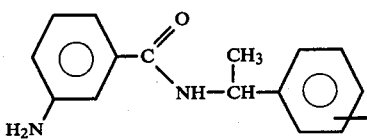

Names: 3-amino-N—(alpha-methylbenzyl)-benzamide;
[m-amino-N—(alpha-methylbenzyl)-benzamide]

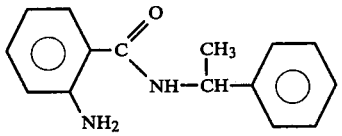

Names: 2-amino-N—(alpha-methylbenzyl)-benzamide;
[o-amino-N—(alpha-methylbenzyl)-benzamide]

SYNTHESIS

These compounds were made by the same 2-step sequence described for 4-amino-N-(alpha-methylbenzyl)-benzamide. A list of the appropriate acid chloride and amine for each compound is given below:

| No. | Acid Chloride | Amine |
|-----|---------------|-------|
| 1 | 4-nitrobenzoylchloride | aniline |
| 2 | " | cyclohexylamine |
| 3 | " | amylamine |
| 4 | " | benzylamine |
| 5 | " | di-n-propylamine |
| 6 | " | n-hexylamine |
| 7 | " | n-butylamine |
| 8 | " | N—methylbenzylamine |
| 9 | 3-nitrobenzoylchloride | alpha-methylbenzylamine |
| 10 | 2-nitrobenzoylchloride | alpha-methylbenzylamine |

BIOLOGICAL DATA ON SIMILAR COMPOUNDS

The available activity data on these similar amino-benzamides is given below:

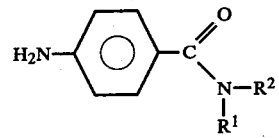

TABLE 9.

| No. | $R^1$ | $R^2$ | Anti-convulsant Data (mg/kg)* | | |
|-----|-------|-------|------|------|------|
| | | | TD50 | ED50 MES | ED50 sc Met |
| 1 | H | —$C_6H_5$ | 111.30 | 50.54 | 59.11 |
| 2 | H | —$C_6H_{12}$ | 188.56 | 67.18 | 123.34 |
| 3 | H | —$(CH_2)_4CH_3$ | 68.55 | 42.98 | 57.27 |
| 4 | H | —$CH_2$—$C_6H_5$ | 83.44 | 23.30 | — |
| 5 | —$CH_2CH_2CH_3$ | —$CH_2CH_2CH_3$ | 115.54 | 61.66 | — |
| 6 | H | —$(CH_2)_5$—$CH_3$ | Activity at 100 mg/kg or less | | |
| 7 | H | —$(CH_2)_3$—$CH_3$ | Activity at 100 mg/kg or less | | |
| 8 | $CH_3$ | —$CH_2$—$C_6$—$H_5$ | Activity at 100 mg/kg or less | | |
| 9 | 3-amino-N—(alpha-methylbenzyl)benzamide-m-amino-N—(alpha-methylbenzyl)-benzamide | | Activity at 100 mg/kg or less | | |
| 10 | 2-amino-N—(alpha-methylbenzyl)benzamide-o-amino-N—(alpha-methylbenzyl)-benzamide | | Activity at 100-300 mg/kg | | |

*all data obtained by i.p. administration in mice

As can be seen from Table 9, these other amino-benzamide compounds have similar activities to those of 4-amino-N-(alpha-methylbenzyl)-benzamide. It is felt that they may be substituted as indicated above for the first compound and should have similar toxicity and absorption levels. It is, therefore, apparent from the above Tables and Examples that these compounds may be substituted for one another and used in similar manner.

With regard to dosage levels for human beings, it can be seen from the differences in dosage levels per kilogram weight used for mice versus that used for rats that when dealing with human beings it would be necessary to determine this level by testing over a wide range using very small amounts worked up to larger amounts and the level is then determined by the side-effects and its activity.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the mete and bounds of the claims or that form their functional as well as conjointly cooperative equivalent are, therefore, intended to be embraced by those claims.

I claim:

1. A method of treating epilepsy and other convulsive disorders comprising administering an N-substituted amino-benzamide selected from the group consisting of 4-amino-N-phenyl-benzamide, 4-amino-N-cyclohexyl-benzamide, 4-amino-N-amyl-benzamide, 4-amino-N-benzyl-benzamide, 4-amino-N,N-(di-n-propyl)-benzamide, 4-amino-N-(n-hexyl)-benzamide, 4-amino-N-(n-butyl)-benzamide, 3-amino-N-(alpha-methylbenzyl)-benzamide, 2-amino-N-(alpha-methylbenzyl)-benzamide, and 4-amino-N-(alpha-methylbenzyl)-benzamide.

2. The method of claim 1 wherein the benzamide is administered subcutaneously in an effective amount.

3. The method of claim 1 wherein the benzamide is administered intraperitoneally in an effective amount.

4. The method of claim 1 wherein the benzamide is administered orally in an effective amount.

5. 4-amino-N-(alpha-methylbenzyl)-benzamide.

* * * * *